(12) United States Patent
Wang

(10) Patent No.: US 11,890,056 B2
(45) Date of Patent: Feb. 6, 2024

(54) METHOD FOR STANDARDIZED OPHTHALMIC FUNDUS IMAGING FOR THE LONGITUDINAL MONITORING OF PATIENTS WITH EYE DISEASES

(71) Applicant: TECHEVERST CO., LTD., Taipei (TW)

(72) Inventor: Victoria Y Wang, Taipei (TW)

(73) Assignee: TECHEVERST CO., LTD., Taipei (TW)

( * ) Notice: Subject to any disclaimer, the term of this patent is extended or adjusted under 35 U.S.C. 154(b) by 554 days.

(21) Appl. No.: 17/117,980

(22) Filed: Dec. 10, 2020

(65) Prior Publication Data
US 2021/0366134 A1   Nov. 25, 2021

(30) Foreign Application Priority Data
May 22, 2020 (TW) .................................. 109117213

(51) Int. Cl.
| | |
|---|---|
| *A61B 3/15* | (2006.01) |
| *G06T 7/33* | (2017.01) |
| *G06T 7/00* | (2017.01) |
| *A61B 3/00* | (2006.01) |
| *A61B 3/14* | (2006.01) |
| *A61B 3/12* | (2006.01) |
| *G06V 10/75* | (2022.01) |
| *G06V 10/25* | (2022.01) |
| *G06V 40/18* | (2022.01) |

(52) U.S. Cl.
CPC ............ *A61B 3/152* (2013.01); *A61B 3/0041* (2013.01); *A61B 3/0091* (2013.01); *A61B 3/12* (2013.01); *A61B 3/14* (2013.01); *G06T 7/0014* (2013.01); *G06T 7/33* (2017.01); *G06V 10/25* (2022.01); *G06V 10/751* (2022.01); *G06V 40/18* (2022.01); *G06T 2200/24* (2013.01); *G06T 2207/30041* (2013.01)

(58) Field of Classification Search
CPC ..... A61B 3/152; A61B 3/0041; A61B 3/0091; A61B 3/12; A61B 3/14; G06T 7/0014; G06T 7/33; G06T 2200/24; G06T 2207/30041; G06T 2207/10056; G06T 2207/30168; G06T 7/0012; G06T 7/73; G06V 10/25; G06V 10/751; G06V 40/18
USPC ......................................................... 351/206
See application file for complete search history.

(56) References Cited

U.S. PATENT DOCUMENTS

| | | | | |
|---|---|---|---|---|
| 2004/0258285 | A1* | 12/2004 | Hansen ................. | G06T 7/0012 382/128 |
| 2010/0208204 | A1* | 8/2010 | Imamura ............... | G16H 50/20 351/246 |
| 2012/0007964 | A1* | 1/2012 | Morisada ............. | H04N 13/128 348/54 |

(Continued)

*Primary Examiner* — Mohammed A Hasan
(74) *Attorney, Agent, or Firm* — MUNCY, GEISSLER, OLDS & LOWE, P.C.

(57) ABSTRACT

The present invention provides a method to consistently and continuously monitor an individual's ocular fundus via the acquisition of standardized fundus images longitudinally, especially for (but not limited to) individuals with diabetic retinopathy. Briefly, the key points of the present invention include: (a) using an aiming beam to target anatomic landmarks of the ocular fundus; (b) using normal anatomic landmarks as registration points; (c) providing a method of image acquisition to create standardized images.

7 Claims, 6 Drawing Sheets

(56) References Cited

U.S. PATENT DOCUMENTS

| | | | |
|---|---|---|---|
| 2012/0229765 A1* | 9/2012 | Makihira | A61B 3/102 |
| | | | 351/246 |
| 2012/0328156 A1* | 12/2012 | Nakano | G06T 7/12 |
| | | | 382/103 |
| 2013/0004046 A1* | 1/2013 | Nakano | G06T 7/13 |
| | | | 382/131 |
| 2014/0327917 A1* | 11/2014 | Sato | A61B 3/102 |
| | | | 356/479 |

* cited by examiner

METHOD FOR STANDARDIZED OPHTHALMIC FUNDUS IMAGING FOR THE LONGITUDINAL MONITORING OF PATIENTS WITH EYE DISEASES

BACKGROUND OF INVENTION

1. Field of the Invention

The present invention provides a method to continuously and consistently monitor patients' ocular fundus images. This system can be used in conjunction with a mobile device/funduscope capable of capturing fundus images; it is especially useful for monitoring patients with retinal disorders, such as diabetic retinopathy (DR), to detect early signs of worsening.

2. Description of Related Art

DR is the leading cause of blindness in middle-aged adults (20-74 years) in developed countries. As diabetes mellitus continues to rise in prevalence, DR has also become a major public health concern. In particular, diabetic macular edema (DME), a sight-threatening complication of DR, affects nearly 30% of individuals with more than 20 years of diabetes.

Patients with early-stage DR may not have any symptoms. In general, 30% of patients with a 10-year history of diabetes have fundus lesions, and up to 80% of patients with a 25-year history of diabetes have fundus lesions.

The pathogenesis of DR stems from chronic hyperglycemia, which injures the endothelium of retinal blood vessels, inducing the formation of a series of fundus lesions. Known accelerators of DR progression include poor glycemic control, insulin dependence, hypertension, hyperlipidemia, and renal dysfunction.

Currently, the diagnosis of DR is made via OCT/fluorescence angiography. DR is staged as follows based on the progression of funduscopic features: (1) Mild Nonproliferative Retinopathy (NPDR); (2) Moderate NPDR; (3) Severe NPDR; (4) Proliferative Retinopathy (PDR), hence funduscopic examination is an important component of diabetic eye care. During a dilated eye exam, the pupil is dilated via eye drops, and the ophthalmoscope and slit lamp are used to check for the presence of vascular proliferation or other lesions in the fundus. This is a time consuming process that may be uncomfortable and inconvenient for patients, contributing to lower follow up rates. In addition, there are often variations in recording examination results, which makes it difficult to objectively compare DR disease progression longitudinally. Furthermore, dilated eye exams are usually performed by an ophthalmologist in the office, but in medically underserved areas with sparse hospitals and resources, it is challenging for patients to go to hospitals for regular eye care.

SUMMARY OF THE INVENTION

Therefore, the purpose of the present invention is to provide a system that allows diabetic patients to track their DR disease progression continuous and consistently, from the comfort of their home. This system allows users to capture standardized, high definition fundus photographs at home, and provides a reliable and convenient method for patients to record photographs of their fundus longitudinally. This makes it feasible to compare changes in patients' fundus photographs across time.

By comparing patients' recent fundus photographs with previous ones, either ophthalmologists or trained AI systems can identify new features or changes that indicate DR disease progression.

In summary, the present invention provides a novel method to take standardized ophthalmic fundus photographs, including (a) using an aiming beam to target anatomic landmarks of the fundus; (b) using normal anatomic landmarks as registration points; (c) providing a method of image acquisition to create standardized images. Thus, the present invention provides an efficient method to continuously and consistently monitor DR patients' ocular fundus for analysis. Disease progression can be identified through the comparison of longitudinal images. Of importance, it should be noted that though this invention is explained in terms of DR, it is not limited to only DR, and can be used to monitor other retinal diseases as well.

DETAILED DESCRIPTION OF THE INVENTION

Figure 1:
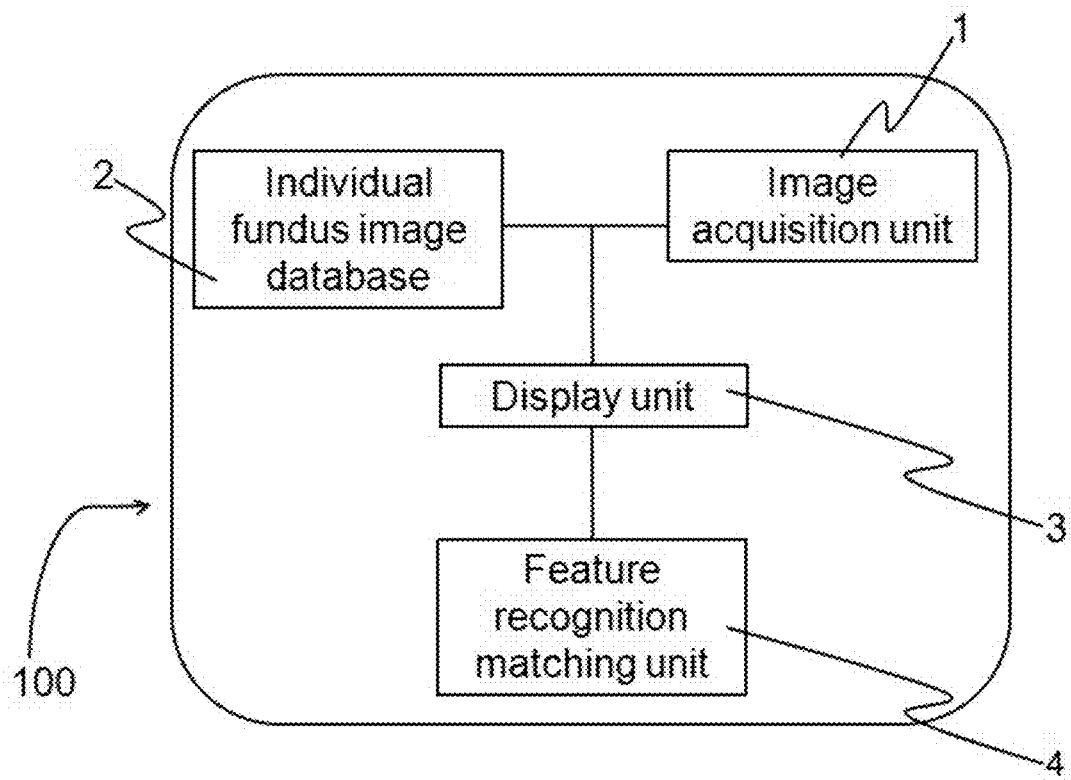
FIG. 1 is the block diagram of the ophthalmoscopic examination device of the present invention.

The technical content of the present invention is described below by specific implementation patterns. Those familiar with this discipline can understand the advantages and effects of the present invention according to the content disclosed in this specification. However, the present invention can be practiced or applied in different forms of patterns without deviating from the spirit of the present invention.

In an embodiment of the present invention, the term "individual" used in this application refers to a user, an operator, especially a diabetic patient. In another embodiment, the present invention can be operated by a diabetic in the home environment, or be operated by a diabetic with others' assistance in the home environment. In addition, the individual can perform fundus image acquisition confirmation for the contralateral eye after fundus image acquisition confirmation for a given eye.

As disclosed in FIGS. 1-8, the present invention provides an ophthalmoscopic examination device 100 to continuously and consistently monitor patients' ocular fundus images, for example (but not limited to), providing an individual who has diabetic retinopathy a method for standardized fundus imaging in order to continuously monitor DR progression. The ophthalmoscopic examination instrument 100, 100a includes, but is not limited to, a mobile device, a funduscope, in conjunction with a mobile device/funduscope. In one embodiment, a mobile device is selected from a smart mobile hand-held monitoring device 101a, 101b. The ophthalmoscopic examination instrument 100 at least comprises an image acquisition unit 1, an individual fundus image database 2, a display unit 3 and a feature recognition matching unit 4 (please refer to FIG. 1). The image acquisition unit 1, individual fundus image database 2, display unit 3 and feature recognition matching unit 4 can be disposed in a smart mobile hand-held monitoring device 101a, 101b and be electrically connected to each other. The image acquisition unit 1 can be used to capture an image to be identified; the image to be identified is a standardized fundus image in the focal length of an image acquisition unit. The individual fundus image database can be used to store a "fundus filing image." The fundus filing image uses the Fovea and Optic cup of fundus of the patient with diabetic retinopathy as two registration points. For example, Fovea F or Macula Ma can be the first registration point R1, Optic disc Od or Optic cup Oc can be the second registration point R2 (please refer to FIG. 3C, FIG. 6, FIG. 7). The display unit 3 has a "ringed target center" C which is displayed and projected by the image acquisition unit 1 (please refer to FIG. 5), and the "fundus zone" is identified (circled) by the ringed target center on the fundus image. The feature recognition matching unit 4 can calculate whether the fundus zone and fundus filing image have sufficient overlapping area (based on a standard value). If not, the smart mobile device sends an error message, for example, but not limited to, an error message displayed by the display unit, such as an image or sound. Furthermore, the ringed target center C is provided with at least a virtual target; the virtual target can be ring shaped, cross-ring shaped, or triangular. For example, the first virtual target T1 could be aligned with the Optic cup of the fundus, and the second virtual target T2 could be aligned with the Fovea of the fundus (please refer to FIG. 6).

In another embodiment of the present invention, in order to follow disease progression longitudinally, the present invention provides a method to capture standardized fundus images. In terms of the steps, the image acquisition unit is moved to a test position to image the fundus of the individual. The test position is anterior to the eye of the individual. The use of an aiming beam is the key first step to standardizing fundus images in this invention. The eye of an individual is aligned via the aiming beam. In other words, the individual's eye is aligned and positioned when it focuses on the aiming beam 51 emitted from a light source 5; the light source 5 can be positioned in a smart mobile hand-held monitoring device. To reiterate, the individual can align their eye E by directly looking at the target beam emitted from the image acquisition unit 1 (e.g. lens) of the smart mobile hand-held monitoring device (i.e. hand-held smart device or mobile phone) of the present invention, then the aiming beam 51a, 51b passes through the lens to focus on the retina Rt to form an aiming beam spot 511 (please refer to FIG. 3C).

Figure 2:
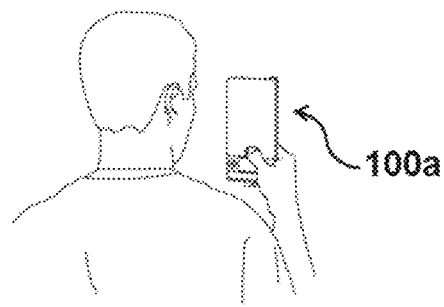
FIG. 2 illustrates a diagram of the ophthalmoscopic examination device operated by an individual in one embodiment of the present invention.
Figure 3A:
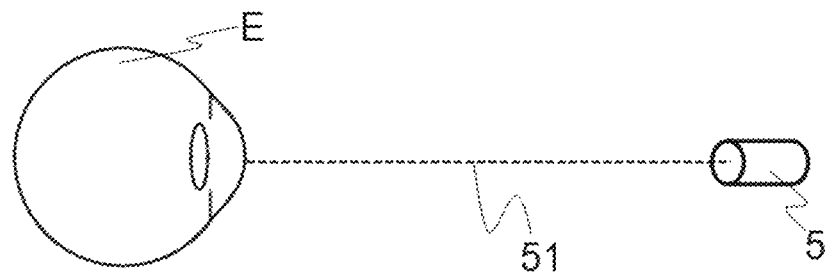
FIG. 3A diagrams the use of an aiming beam to target one eye of an individual, in another embodiment of the present invention.
Figure 3B:
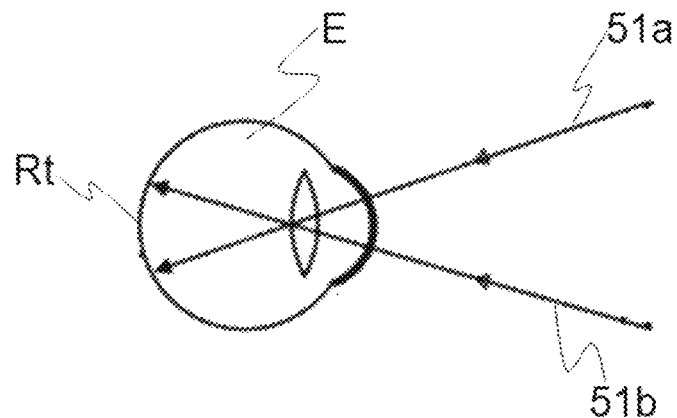
FIG. 3B diagrams the use of an aiming beam to target one eye of an individual, in another embodiment of the present invention.
Figure 3C:
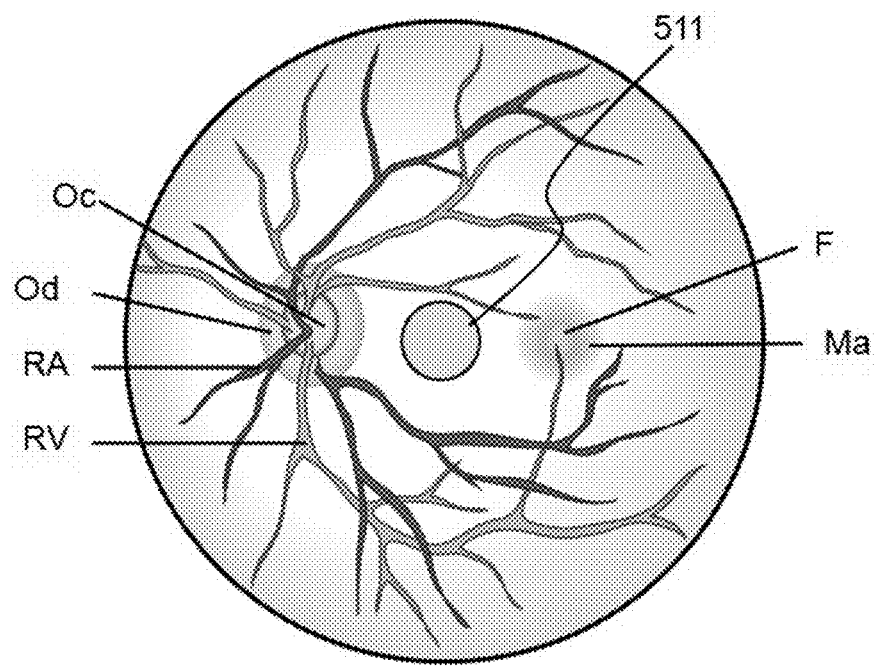
FIG. 3C diagrams the use of an aiming beam in targeting anatomic landmarks in the eye of an individual, in another embodiment of the present invention.
Figure 4:
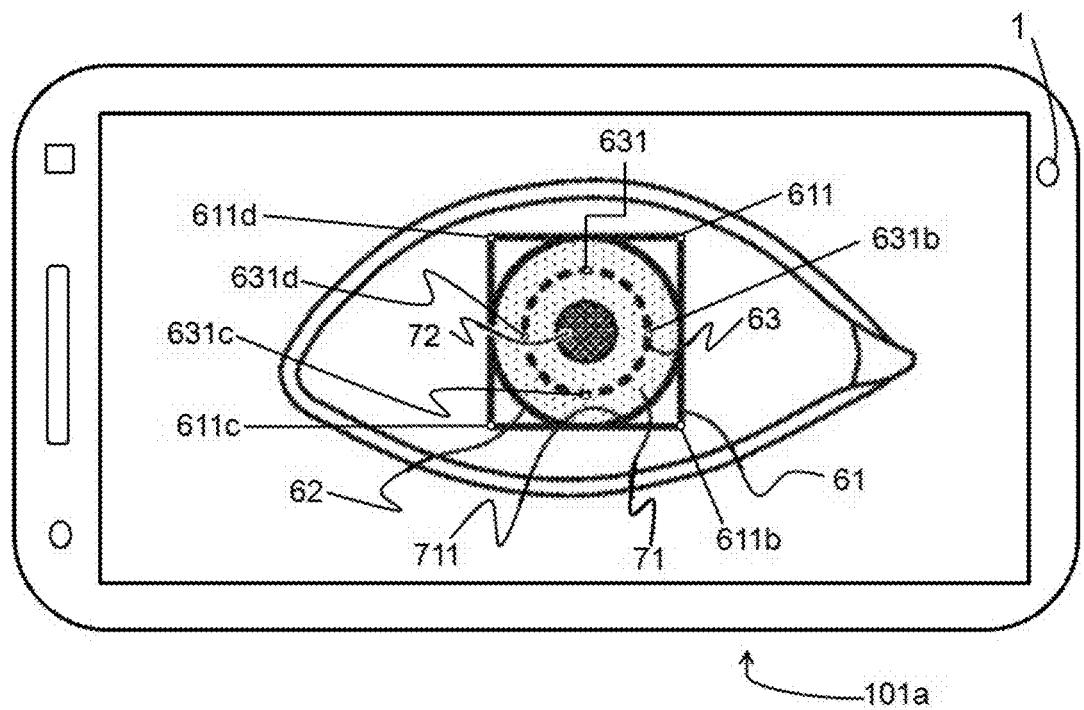
FIG. 4 illustrates a diagram for operating the ophthalmoscopic examination device in another embodiment of the present invention.
Figure 5:
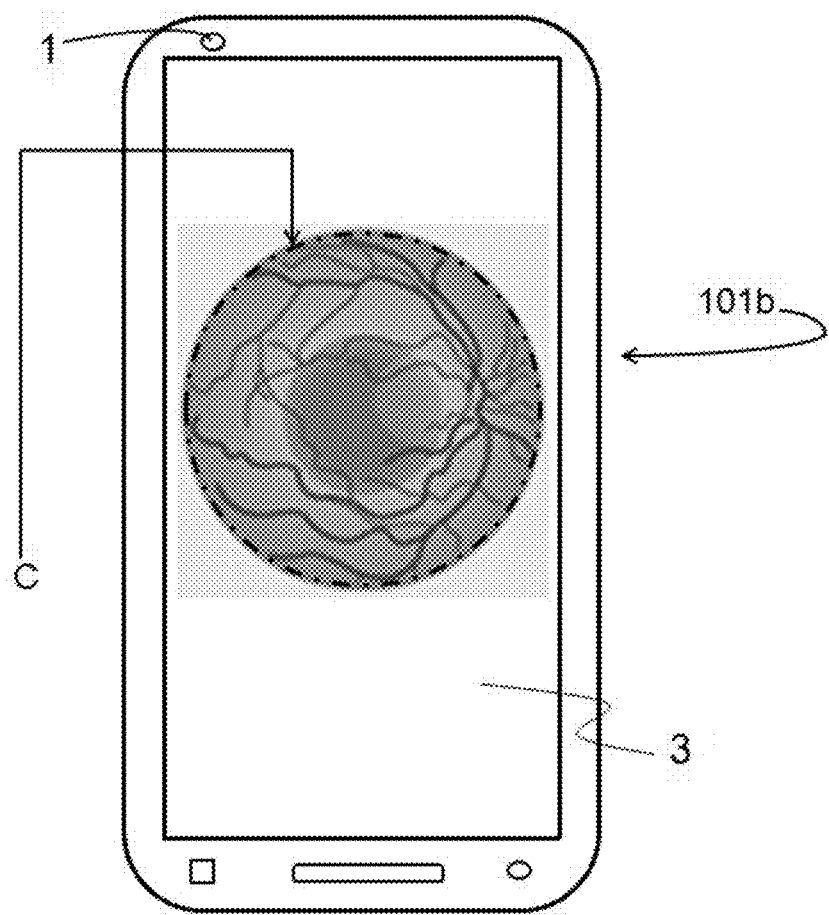
FIG. 5 illustrates a diagram for operating the ophthalmoscopic examination device in another embodiment of the present invention.
Figure 6:
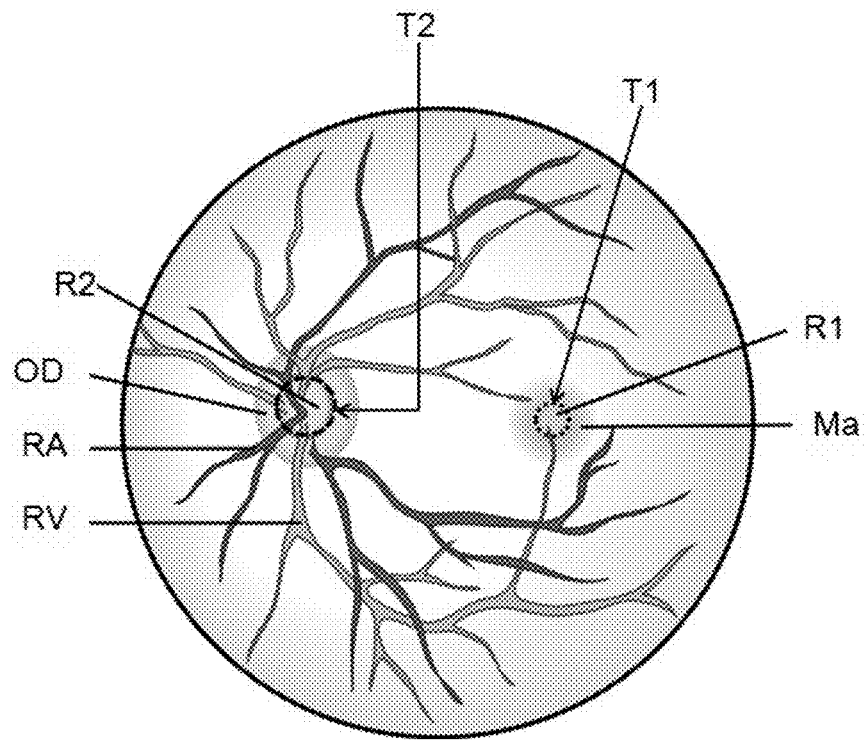
FIG. 6 illustrates a diagram for operating the ophthalmoscopic examination device in another embodiment of the present invention.
Figure 7:
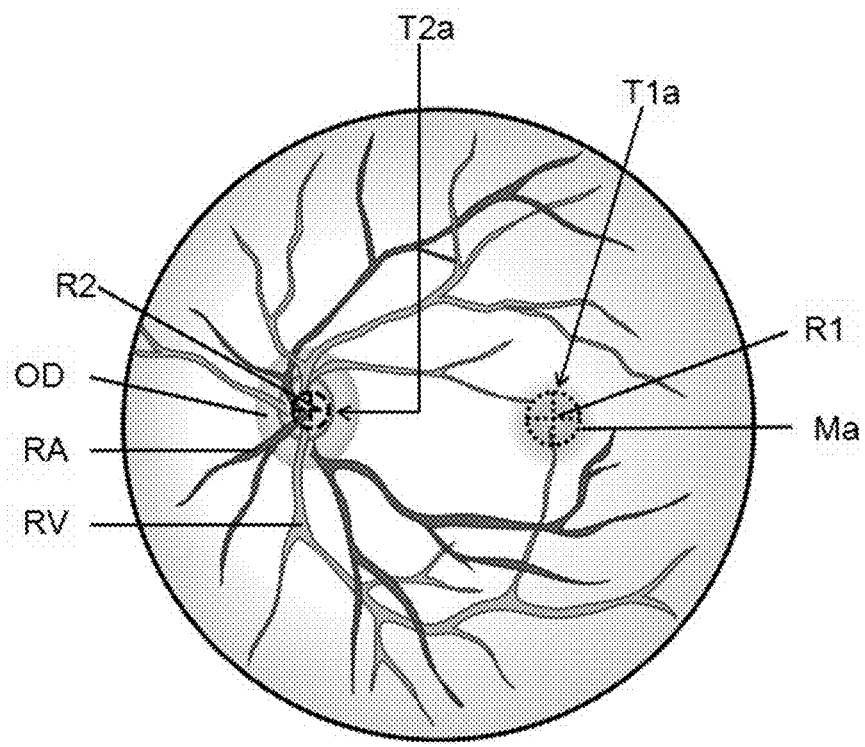
FIG. 7 illustrates a diagram for operating the ophthalmoscopic examination device in another embodiment of the present invention.
Figure 8:
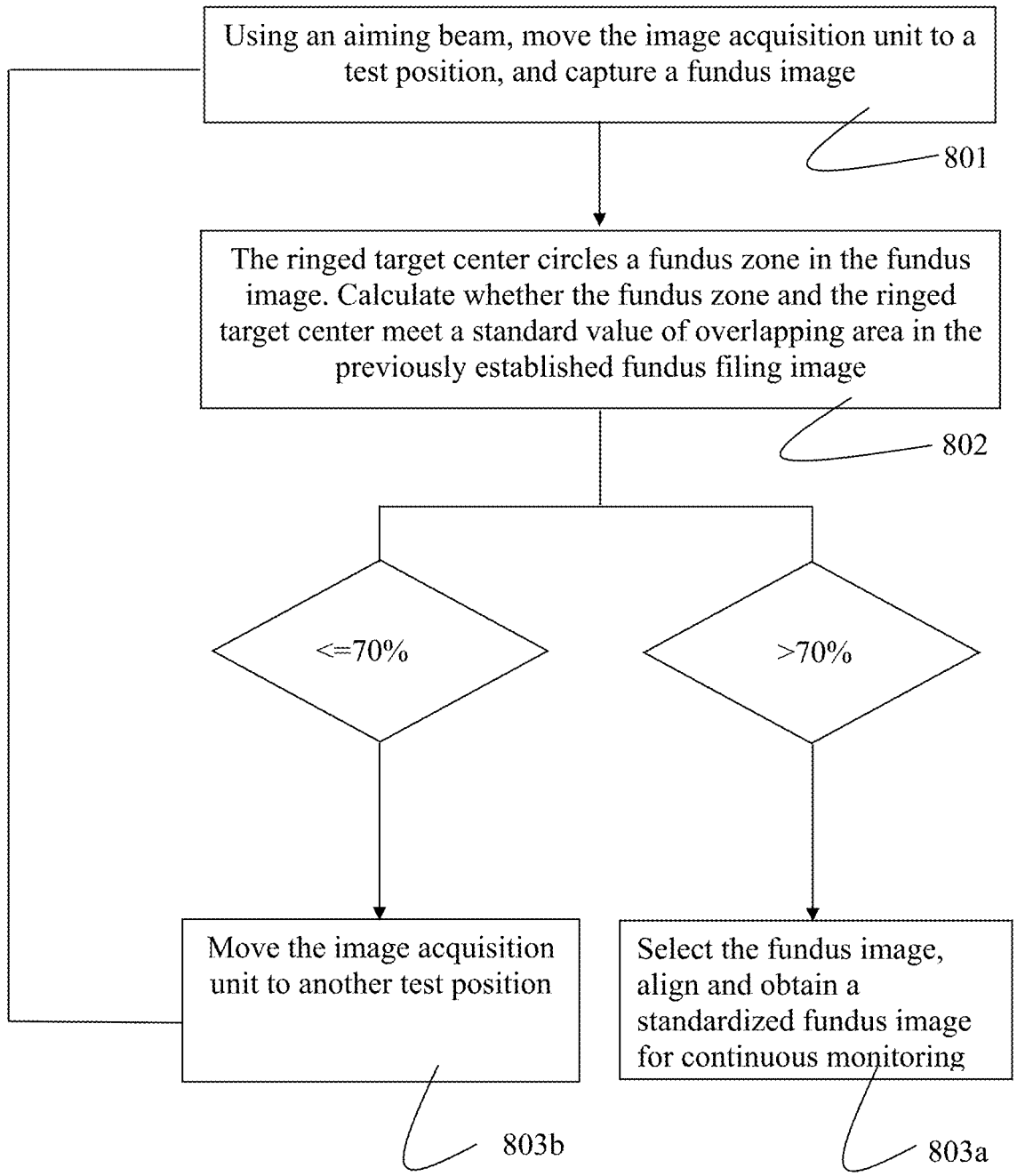
FIG. 8 is a flow diagram showing the present invention's steps of standardized fundus image acquisition.

By looking directly at the target beam, the individual's eyeball alignment/direction is standardized (please refer to FIG. 2, FIG. 3A, FIG. 3B). Meanwhile, the image of the individual's eye and the image of the target light can be transmitted to the display unit 3 (please refer to FIG. 5). In other words, the target light serves to standardize the eyeball alignment of the individual by a virtual sight locating piece 61 in the display unit 3, for example, but not limited to standardizing the cornea 71 of the individual. Furthermore, in another embodiment of the present invention, a virtual sight locating piece 61 is provided with a virtual locating point 611; the virtual locating point 611 can be located at the four corners of the virtual sight locating piece 61. Certainly, the present invention is not limited to this, in other embodiments of the present invention, there can be an elliptic virtual sight locating piece 62, a ring virtual sight locating piece 63 and a ring virtual locating point 631, wherein the elliptic virtual sight locating piece can be aligned with the corneal margin 711 of an individual, and the ring virtual sight locating piece 63 can be aligned between the cornea 71 and pupil 72 of the individual (please refer FIG. 4).

In another embodiment of the present invention, the steps for standardized fundus imaging in order to continuously and consistently monitor patients' fundus images include the following: (a) the image acquisition unit of the ophthalmoscopic examination instrument 100a is moved to a test position, which is in front of the eye of a patient, which is to say, the test position places the fundus of the patient in the focal length of an image acquisition unit, and a fundus image is captured (step 801). The image acquisition unit provides a ringed target center, and the fundus image can be transmitted to the display unit 3 of smart mobile hand-held monitoring device 101b (please refer to FIG. 5).

Moreover, the present invention's method to standardize fundus imaging includes the following: (b) a fundus zone is circled by the ringed target center C in the fundus image (please refer to FIG. 5), and the ringed target center provides at least two virtual targets. In the aforementioned step, the fundus image has at least two reference coordinates, one of the reference coordinates is selected from the fovea F, and the other one is selected from the optic cup Oc. The virtual targets are aligned with the reference coordinates respectively to obtain the standardized ocular fundus image, e.g. the standardized fundus image for continuously and consistently monitoring DR patients' ocular fundus.

Certainly, the present invention is not limited to this, wherein the reference coordinates include the retinal vein and retinal artery of the patient with DR, the retinal vein and the arteria retina include venula temporalis retinae superior, venula nasalis retinae superior, venula nasalis retinae inferior, venula temporalis retinae inferior, arteriola temporalis retinae superior, arteriola nasalis retinae superior, arteriola nasalis retinae inferior, arteriola temporalis retinae inferior.

Preferably, the method provided by the present invention uses the contrast value of the fundus image to define the fundus margin to circle the fundus zone, and calculates whether the fundus zone and the ringed target center meet a standard value of overlapping area in the previously established fundus filing image (step 802). In another embodiment, the coverage of the ringed target center can show whether the captured fundus image deviates from the target center or not. At the same time, it can also show whether an appropriate focal plane exists between the image acquisition unit and the individual's fundus.

In one embodiment, 70% is selected as the standard value; i.e. greater than 70% overlap between the areas of the fundus zone and the ringed target center is required. In another embodiment, the standard value of overlapping area is set at 80%. In yet another embodiment, the standard value is set between 90% to 95%. In other words, if the overlapping area does not meet the standard value, the patient/user can perform manual regulation according to the visual/auditory prompt emitted by the smart mobile device. Furthermore, the built-in software of the smart mobile device performs automatic focusing; the steps include the following:

(c) If in the aforementioned step (b), the fundus zone and the previously established fundus filing image meet the standard value of overlapping area after calculation, the fundus image can be selected and aligned to obtain the standardized fundus image (step 803a);

On the other hand, if in the aforementioned step (b), the fundus zone and the previously established fundus filing image do not meet the standard value of overlapping area after calculation, the patient/user can use the difference in the overlapping area to evaluate the focal length in relation to the fundus, and move to another position in the focal plane (step 803b), then repeat steps (a) to (b) until the fundus filing image meets the standard value of overlapping area.

In summary, in the present invention's proposed method to capture standardized fundus images, the use of an aiming beam is the key first step, as the eye of an individual is aligned via the aiming beam. By gazing directly at the target light emitted from the smart mobile hand-held monitoring device, an individual's eye alignment is standardized. In addition, the fovea and optic cup can be used as reference coordinates to capture standardized fundus images, so that over time, patients can obtain a series of longitudinal, standardized fundus images from the comfort of their home. These images can then be transmitted to and evaluated by an ophthalmologist/AI system in real time, thus allowing for the continuous and consistent monitoring of retinal features such as microbleeds, hard exudates, petechial hemorrhage, neovascularization, and cotton wool spots effectively.

Although this invention has been explained in relation to its preferred embodiment, it is to be understood that many other possible modifications and variations can be made without departing from the spirit and scope of the invention as hereinafter claimed.

The invention claimed is:

1. A method to continuously and consistently monitor an individual's ocular fundus, by enabling an acquisition of standardized fundus images, the method comprising:
   (a) using an aiming beam to align and target registration points;
   (b) moving an image acquisition unit disposed in an ophthalmoscopic examination instrument to a first test position, wherein the first test position places the individual's fundus in a focal length of the image acquisition unit, and capturing a fundus image;
   (c) wherein the image acquisition unit has a ringed target center calculating whether a fundus zone and the ringed target center meet a standard value of overlapping area in a previously established fundus filing image by circling the fundus zone by the ringed target center in the fundus image;
   (d) obtaining a standardized fundus image by aligning if a result of the aforementioned step (c) is affirmative; and
   (e) moving the image acquisition unit to a second test position by calculating a difference of the fundus filing image if the result of step (c) is negative, and repeating steps (a) to (b) until the fundus filing image meets the standard value of overlapping area,
   wherein the standard value of overlapping area is at least 70%.

2. The method of claim 1, wherein the ringed target center has at least two virtual targets, wherein the fundus image has at least two reference coordinates, wherein one of the reference coordinates is selected from the central fovea of the individual, and the other one is selected from the optic cup of the individual, wherein the virtual targets are aligned with the reference coordinates respectively to obtain the standardized fundus image.

3. The method of claim 2, wherein a fundus margin is defined by a contrast value of the fundus image to circle the fundus zone.

4. The method of claim 3, wherein the reference coordinates include retinal vein and retinal artery of the individual, wherein the retinal vein and the retinal artery include venula temporalis retinae superior, venula nasalis retinae superior, venula nasalis retinae inferior, venula temporalis retinae inferior, arteriola temporalis retinae superior, arteriola nasalis retinae superior, arteriola nasalis retinae inferior, and arteriola temporalis retinae inferior.

5. The method of claim 1, wherein in step (a), to capture the fundus image of the individual, an eye of the individual is aligned and positioned by the aiming beam, so as to standardize the individual's eye alignment.

6. An ophthalmoscopic examination device for acquiring standardized fundus images to continuously and consistently monitor ocular fundus, comprising:
   an image acquisition unit, for capturing an image to be identified, wherein the image to be identified is a standardized fundus image in a focal length of an image acquisition unit;
   an individual fundus image database, for storing a fundus filing image, wherein the fundus filing image uses the Fovea and Optic cup of fundus of an individual as two registration points;
   a display unit, electrically connected to the image acquisition unit and the individual fundus image database, with a ringed target center displayed and transmitted from the image acquisition unit, wherein a fundus zone is circled in the fundus image;
   a feature recognition matching unit, electrically connected to the display unit, wherein the feature recognition matching unit calculates whether the fundus zone and the fundus filing image meet a standard value of overlapping area, wherein the standard value of overlapping area is at least 70%, if not, the instrument provides an error message,
   wherein the device sends the error message, then is moved to a second test position after calculating difference of the fundus filing image.

7. The device of claim 6, wherein the ringed target center is provided with a virtual target and the virtual target is ring shaped, cross ring shaped or triangular.

* * * * *